United States Patent
Yamazaki et al.

(10) Patent No.: US 8,012,327 B2
(45) Date of Patent: Sep. 6, 2011

(54) CAPILLARY ELECTROPHORESIS APPARATUS AND ELECTROPHORESIS METHOD

(75) Inventors: Motohiro Yamazaki, Mito (JP); Ryoji Inaba, Hitachinaka (JP); Satoshi Takahashi, Hitachinaka (JP); Isao Haraura, Hitachinaka (JP); Tomoyuki Sakai, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 970 days.

(21) Appl. No.: 11/653,332

(22) Filed: Jan. 16, 2007

(65) Prior Publication Data

US 2007/0163882 A1  Jul. 19, 2007

(30) Foreign Application Priority Data

Jan. 16, 2006  (JP) ................... 2006-007867

(51) Int. Cl.
*G01N 27/447* (2006.01)
(52) U.S. Cl. ......... 204/452; 204/603; 204/601; 356/344
(58) Field of Classification Search ............... 204/252, 204/452, 601, 603; 356/344, 432, 444, 433–443
See application file for complete search history.

(56) References Cited

U.S. PATENT DOCUMENTS

| 6,508,923 B1* | 1/2003 | Hayashizaki et al. ........ 204/603 |
| 6,821,402 B1 | 11/2004 | Sharaf et al. |
| 6,863,791 B1 | 3/2005 | Liu et al. |
| 6,936,152 B2* | 8/2005 | Kojima et al. ................ 204/601 |
| 2003/0178312 A1 | 9/2003 | Amirkhanian et al. |
| 2004/0072335 A1* | 4/2004 | Boege et al. ............... 435/287.2 |

FOREIGN PATENT DOCUMENTS

| JP | 03-264859 | 11/1991 |
| JP | 5-52810 A | 3/1993 |
| JP | 2833119 | 10/1998 |

* cited by examiner

*Primary Examiner* — Kaj K Olsen
*Assistant Examiner* — Susan Thai
(74) *Attorney, Agent, or Firm* — McDermott Will & Emery LLP

(57) ABSTRACT

An object of the present invention is to provide a capillary electrophoresis apparatus in which simultaneity can be ensured between sensitivity and data acquisition to decrease a pull-up signal while spectral data acquisition is eliminated in each capillary exchange. The invention relates to a capillary electrophoresis apparatus in which capillary position shift is detected in each capillary exchange by detecting a capillary position. A capillary position measuring light source is provided in the capillary electrophoresis apparatus of the invention. The capillary is irradiated with light emitted from the capillary position measuring light source, a capillary image is detected with a two-dimensional detector, and thereby a position deviation of the capillary is determined. On the basis of the position deviation of the capillary, a data acquisition area is set in the two-dimensional detector, or a reference fluorescent light spectrum determined from the capillary at the standard position is corrected.

13 Claims, 13 Drawing Sheets

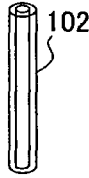
FIG. 9A
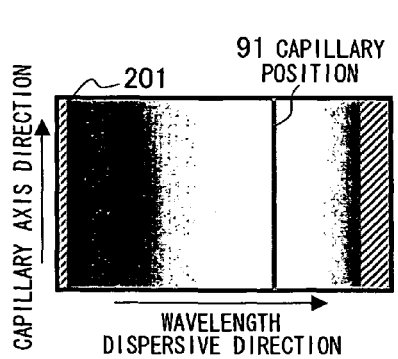
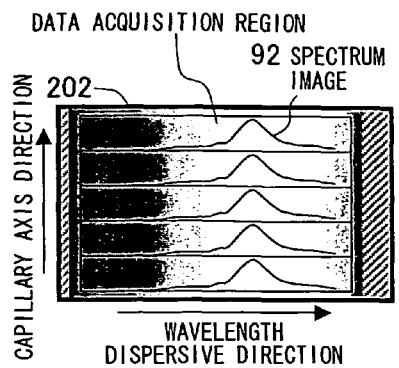
FIG. 9B
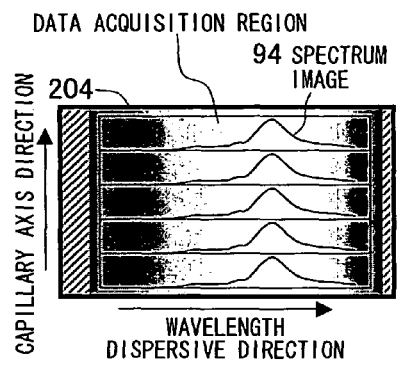
FIG. 9C
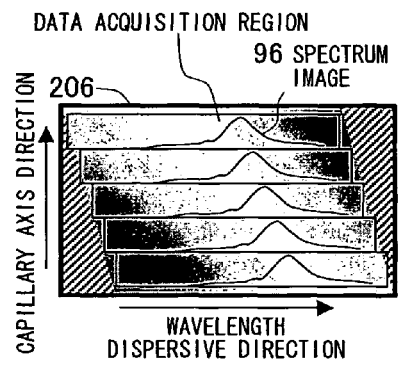
FIG. 9D
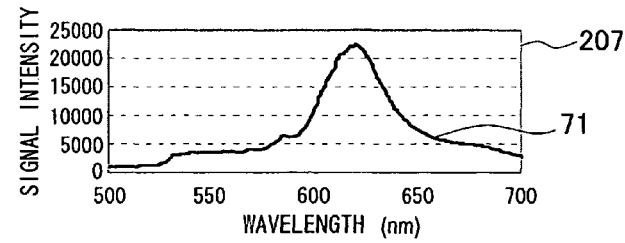
FLUORESCENCE SPECTRUM IMAGE IN DATA ACQUISITION REGION

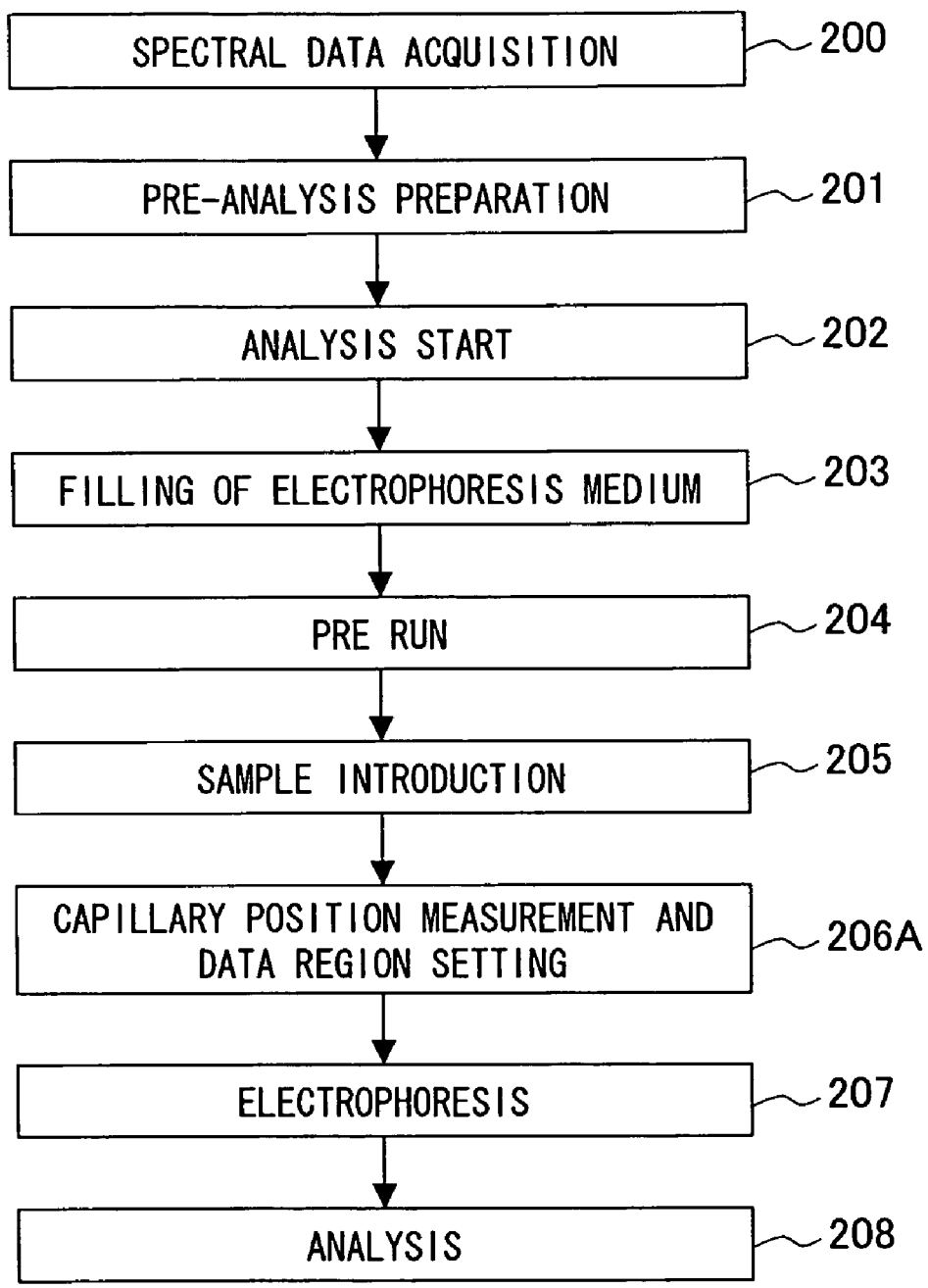

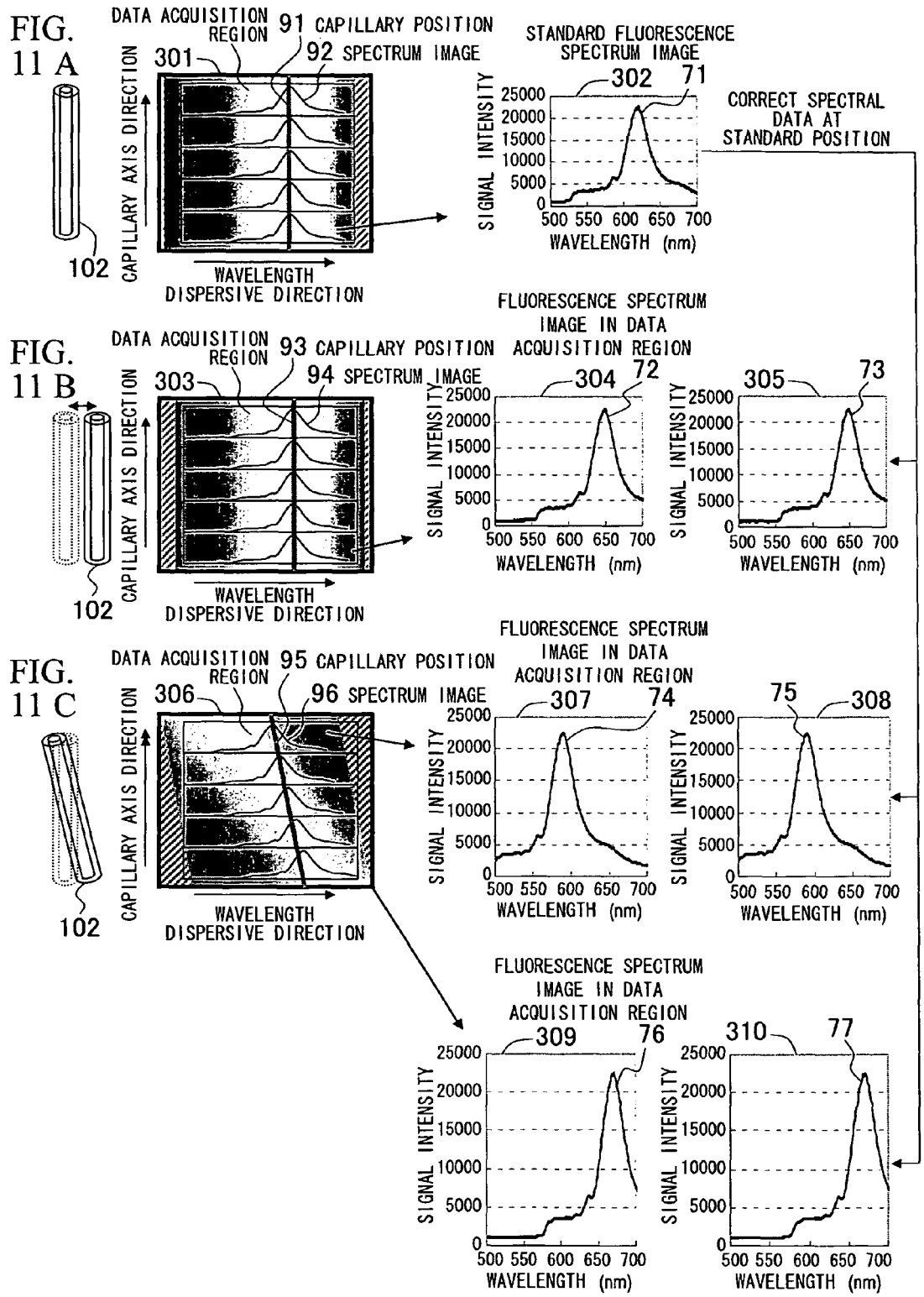

CAPILLARY ELECTROPHORESIS APPARATUS AND ELECTROPHORESIS METHOD

BACKGROUND OF THE INVENTION

1. Field of the Invention

The present invention relates to an electrophoresis apparatus in which nucleic acid, protein, or the like is separated and analyzed by electrophoresis, particularly to a capillary electrophoresis apparatus.

2. Description of the Related Art

Usually a laser light source is used as an excitation light source in the capillary electrophoresis apparatus. However, recently use of a light emitting diode (LED) for the excitation light source is proposed to reduce cost of the capillary electrophoresis apparatus. US 2003/0178312-A1 discloses an electrophoresis apparatus in which LED is used.

Japanese Patent Application Laid-Open No. 5-52810 and Japanese Patent No. 2833119 disclose an electrophoresis apparatus in which the laser beam is not emitted in a direction perpendicular to a capillary axis, but excitation light is emitted in a capillary axis direction. The excitation light propagates through the capillary to excite a detection target substance moving in the capillary without any restriction by a position of the detection target substance. A wide excited region, i.e., a wide detected region is acquired, which allows sensitivity to be enhanced in the electrophoresis apparatus. The detection light from a linear light emission portion is dispersed with a diffraction grating and detected with a two-dimensional detector.

U.S. Pat. Nos. 6,821,402 and 6,863,791 discloses a conventional method of acquiring spectral data.

Earnest study of inventor reveals the following problems. In the technique disclosed in Japanese Patent Application Laid-Open No. 5-52810 and Japanese Patent No. 2833119, because the capillary in itself is used as both an excitation unit and a detection unit, there is generated the problem that a detection position is shifted by capillary exchange. Therefore, it is necessary to acquire spectral data in each capillary exchange. When the spectral data is incorrect, a pull-up signal is generated in an analysis process due to wavelength shift. With increasing wavelength shift, the pull-up signal is increased to reduce reliability of analysis result.

In the spectral data acquiring method disclosed in U.S. Pat. Nos. 6,821,402 and 6,863,791, the actual electrophoresis is required for a known sample, which takes a large amount of time for an operator.

That is, in the method in which the diffraction grating is used, the spectral data acquisition is required in each capillary exchange although the simultaneity can be ensured between the sensitivity and the data acquisition. On the other hand, in the method in which the plural filters are used, the simultaneity cannot be ensured between the sensitivity and the data acquisition although the spectral data acquisition is not required in each capillary exchange.

In view of the foregoing, an object of the invention is to provide a capillary electrophoresis apparatus in which the simultaneity can be ensured between the sensitivity and the data acquisition to decrease the pull-up signal while the spectral data acquisition is eliminated in each capillary exchange.

SUMMARY OF THE INVENTION

The present invention relates to a capillary electrophoresis apparatus in which a capillary position is detected in each capillary exchange to detect capillary position shift.

According to the invention, a capillary electrophoresis apparatus includes a capillary position measuring light source. A capillary is irradiated with light from capillary position measuring light source, and a capillary image is detected with a two-dimensional detector to determine a capillary position deviation.

On the basis of the capillary position deviation, a data acquisition area is set in the two-dimensional detector, or a standard fluorescence spectrum determined from the capillary at a standard position is corrected.

According to the invention, the spectral data acquisition is eliminated in each capillary exchange, and the pull-up signal can be decreased without losing the simultaneity can be ensured between the signal intensity and the signal acquisition.

BRIEF DESCRIPTION OF THE DRAWINGS

FIG. 9 is a view for explaining a first embodiment of an analysis method in which the capillary electrophoresis apparatus is used;

FIG. 10 shows a detailed operation procedure of the first embodiment of the analysis method in which the capillary electrophoresis apparatus is used;

FIG. 11 is a view for explaining a second embodiment of the analysis method in which the capillary electrophoresis apparatus is used;

DETAILED DESCRIPTION OF THE INVENTION

The above and other novel features and advantages of the invention will be described below with reference to the accompanying drawings. However, the drawings are illustrated by way of example only, and the scope of the invention is not limited to the drawings.

Figure 1:
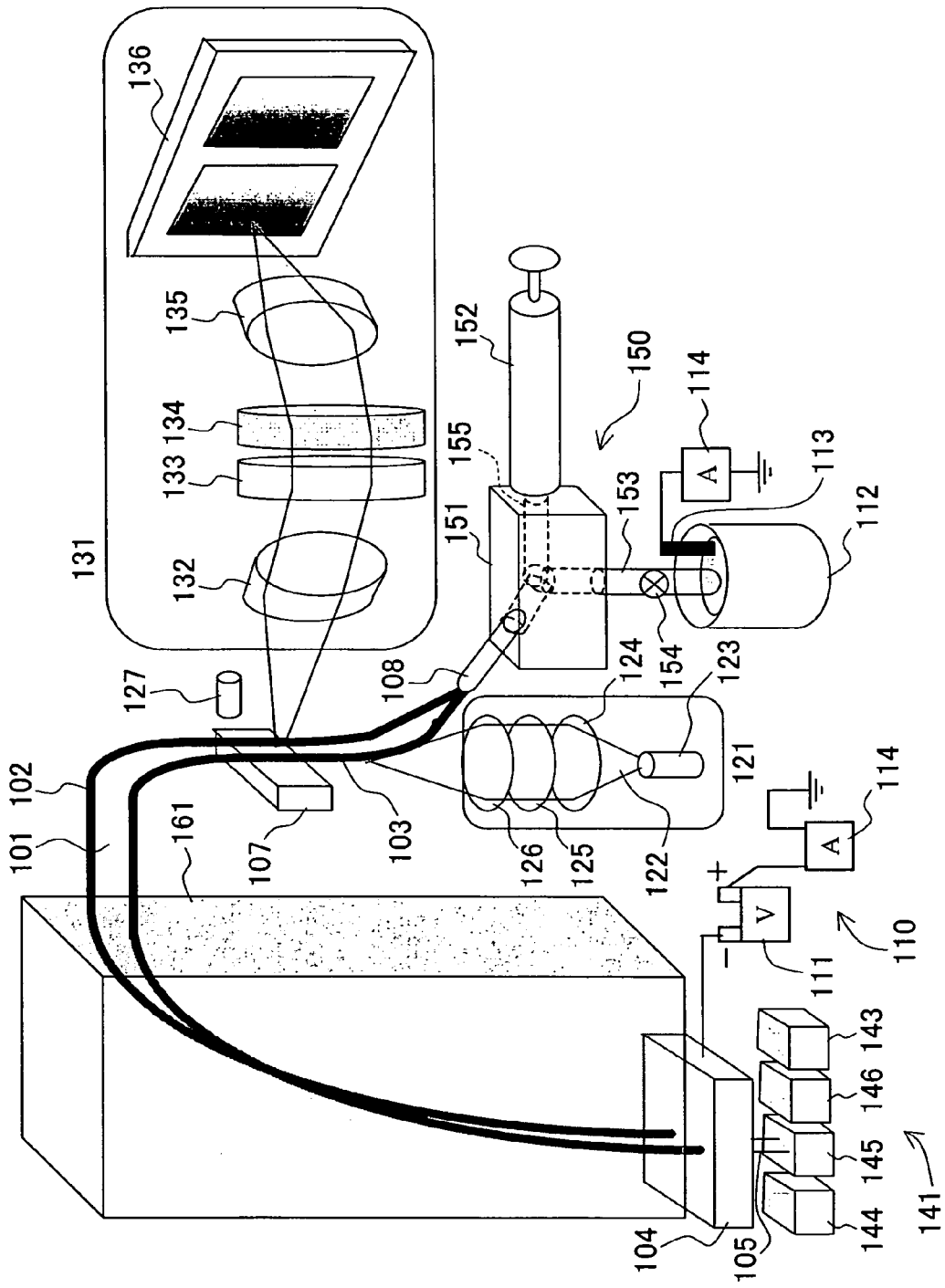
FIG. 1 is a perspective view schematically showing a capillary electrophoresis apparatus.

Referring to FIG. 1A, the capillary electrophoresis apparatus of the embodiment has a capillary array 101, an optical irradiation unit 121, an optical detection unit 131, an automatic sampler unit 141, a pump unit 150, a power supply unit 110, and an oven unit 161. In the capillary electrophoresis apparatus of the embodiment, sample is introduced to each capillary, and sample component in the sample is electrophoresed using plural capillaries filled with electrophoresis mediums. For example, plural samples having DNA containing samples are simultaneously analyzed to analyze base sequence The capillary array 101 includes plural capillaries 102. In FIG. 1, the capillary array 101 includes two capillaries 102. However, for example, the capillary array 101 may include one, four, or eight capillaries 102. The capillary 102 is a thin quartz tube having an inner diameter of tens to hundreds micrometers and an outer diameter of hundreds micrometer, and polyimide coating is performed to a surface of the capillary 102 to enhance strength. Alternatively, fluorine coating may be performed to a portion through the light propagates.

The capillary array 101 is a detachable replacement part which is replaced by a new one when quality is degraded through predetermined-time analyses to decrease separation capacity. The capillary array 101 is exchanged to the capillary array 101 having a different length when a measuring technique is changed to require a change in length of capillary 102. Therefore, the length of the capillary 102 can arbitrarily be adjusted.

The capillary array 101 includes an irradiation unit 103 which is irradiated with the excitation light, a sample introducing end 105 which is used to introduce the sample therethrough, and a capillary head 108 which is formed by bundling the plural capillaries. The sample introducing end 105 is retained by a sample introducing unit 104.

As shown in FIG. 1B, a hollow electrode 106 is inserted into a front edge of the capillary 102, and the front edge of the capillary 102 is slightly projected from the hollow electrode 106. For example, the hollow electrode 106 is formed by a stainless pipe. The capillary head 108 is connected to the pump unit 150.

The optical irradiation unit 121 has a light source 123, a first collective lens 124, an irradiation filter 125, and a second collective lens 126.

In the irradiation unit 103, the capillary 102 is supported on the glass substrate 107. The capillary 102 is irradiated with the excitation light from the optical irradiation unit 121. The light source 123 emits excitation light 122 with which the irradiation unit 103 of the capillary array 101 is irradiated. Usually the laser light source is used as the light source. However, in the embodiment, the light emitting diode (LED) is used as the light source 123.

The first collective lens 124 collects the excitation light 122 of the light source 123. The irradiation filter 125 cuts an unnecessary wavelength component from the excitation light 122. The second collective lens 126 collects the excitation light 122. The capillary 102 is irradiated with the light collected by the second collective lens 126. In the embodiment, the capillary 102 is irradiated with the excitation light while the excitation light is incident along a capillary axis line or while the excitation light is inclined at a predetermined angle with respect to the capillary axis line.

A sample component separated by the electrophoresis in the capillary 102 is irradiated with the excitation light 122. Light having a different wavelength in each sample component is emitted from a fluorescent material labeled to the sample component. The light is detected with the optical detection unit 131.

The optical detection unit 131 has a first camera lens 132, a detection filter 133, a diffraction grating 134, a second camera lens 135, and a two-dimensional detector 136. The optical detection unit 131 will be described in detail later with reference to FIG. 3.

The automatic sampler unit 141 conveys a sample vessel 143, a buffer vessel 144, a cleaning vessel 145, and a waste liquid vessel 146 immediately below the sample introducing unit 104.

The sample vessel 143 is used to hold plural extremely small amount samples, and the sample vessel 143 is conveyed immediately below the sample introducing unit 104 in introducing the sample. For example, the sample is a solution containing a large number of nucleic acids having proper lengths (sizes) fluorescence-labeled by four kinds of nucleotide base molecules.

In the configuration of the sample vessel 143, a scepter which is of a resin sheet is placed on a sample plate including 24-by-16 wells in which the sample of tens microliters can be held in each well, and the scepter is clamped by a holder and a clip. The scepter has through-holes at positions corresponding to the wells, and the through-hole is usually closed to prevent evaporation of the sample in the well. The sample introducing end 105 can come into contact with the sample through the through-hole in introducing the sample. Alternatively, a protective film may adhere to an upper surface of the scepter to prevent evaporation of the sample.

The buffer vessel 144 is used to hold a buffer into which the sample introducing end 105 is dipped, and the buffer vessel 144 is conveyed immediately below the sample introducing unit 104 during the electrophoresis analysis. The buffer vessel 144 is also conveyed immediately below the sample introducing unit 104 in a standby state of the apparatus, and the sample introducing end 105 is dipped in the buffer to prevent the electrophoresis medium in the capillary 102 from drying out.

The cleaning vessel 145 is used to hold a cleaning solution for cleaning the sample introducing end 105, and the cleaning vessel 145 is conveyed immediately below the sample introducing unit 104 during the filling of the electrophoresis medium, during pre run, and after the sample introduction. The sample introducing end 105 is dipped into the cleaning solution in the cleaning vessel, which allows the sample introducing end 105 to be cleaned to avoid contamination.

The waste liquid vessel 146 is used to hold the used electrophoresis medium, and the waste liquid vessel 146 is conveyed immediately below the sample introducing unit 104 during the filling of the electrophoresis medium. During the filling of the electrophoresis medium, the waste liquid vessel 146 receives the used electrophoresis medium discharged from the sample introducing end 105.

The pump unit 150 has a polymer filling block 151, a syringe 152, a tube 153, an electromagnetic valve 154, and an cathode buffer vessel 112. The pump unit 150 fills the capillary 102 with the new electrophoresis medium before the analysis is started.

The polymer filling block 151 has a polymer flow channel 155. The polymer flow channel 155 is communicated with the syringe 152 filled with the electrophoresis medium and with the tube 153 having the electromagnetic valve 154. The other end of the tube 153 is dipped in the buffer held in the cathode buffer vessel 112. The capillary head 108 is attached to the polymer filling block 151 while pressure-resistant airtight is maintained.

The power supply unit 110 includes a high-voltage power supply 111 which generates a high voltage of about 15 kV. A negative electrode of the high-voltage power supply 111 is connected to the hollow electrode 106, and a positive electrode is grounded through an ammeter 114. One end of the cathode electrode 113 is dipped in the buffer in the cathode buffer vessel 112, and the other end is grounded.

The method of filling the capillary 102 with the electrophoresis medium using the pump unit 150 will briefly be described below. The waste liquid vessel 146 is arranged immediately below the sample introducing unit 104, and the electromagnetic valve 154 is closed to push a plunger of the syringe 152. Therefore, the electrophoresis medium in the syringe 152 flows into the capillary 102 from the capillary head 108 through the polymer flow channel 155. The used electrophoresis medium in the capillary 102 is discharged from the sample introducing end 105 and received by the waste liquid vessel 146.

The method of introducing the sample into the capillary 102 will briefly be described below. The capillary 102, the polymer flow channel 155, and the tube 153 are filled with the electrophoresis medium. The sample vessel 143 is arranged immediately below the sample introducing unit 104, the sample introducing end 105 is dipped in the sample held in the well of the sample vessel 143, and the electromagnetic valve 154 is opened. Therefore, an electric current path is formed between the positive electrode and negative electrode of the high-voltage power supply 111. The electric current path consists of the hollow electrode 106, the sample in the sample vessel 143, the electrophoresis path in the capillary 102, the polymer flow channel 155 of the polymer filling block 151, the tube 153, the buffer of the cathode buffer vessel 112, and the cathode electrode 113. The hollow electrode 106 is set at a negative potential while the cathode electrode 113 is set at a positive potential, and a pulse voltage is applied to the electric current path. Therefore, a negatively charged sample component such as DNA existing in the well is introduced to an electrophoresis path from the sample introducing end 105. The sample introducing method is not limited to the electrophoresis, but the sample may be introduced to the electrophoresis path by pressure or divided injection.

During the electrophoresis analysis, the buffer vessel 144 is arranged immediately below the sample introducing unit 104, and the sample introducing end 105 is dipped in the buffer held in the buffer vessel 144. Therefore, an electric current path is formed between the positive electrode and negative electrode of the high-voltage power supply 111. The electric current path consists of the hollow electrode 106, the buffer in the buffer vessel 144, the electrophoresis path in the capillary 102, the polymer flow channel 155 of the polymer filling block 151, the tube 153, the buffer in the cathode buffer vessel 112, and the cathode electrode 113. The hollow electrode 106 is set at a negative potential while the cathode electrode 113 is set at a positive potential, and the high voltage of about 15 kV is applied to the electric current path. Therefore, an electric field is generated in a direction from irradiation unit 103 to the sample introducing unit 104, and the negatively charged sample component introduced into the electrophoresis path is electrophoresed toward the direction of the irradiation unit 103.

The oven unit 161 controls a temperature of the electrophoresis path which has an influence on an electrophoresis speed of the sample component. In the embodiment, the oven unit accommodates the capillaries 102 in a temperature controlled oven (not shown). Air whose temperature is kept constant by a temperature control mechanism such as a Peltier device is circulated in the temperature controlled oven to maintain the capillary 102 at a predetermined temperature by a blower mechanism such as a fan.

In the embodiment, a capillary position measuring light source 127 is provided between the optical detection unit 131 and the glass substrate 107 in which the capillaries 102 are arrayed. The capillary position measuring light source 127 is a light source which emits the light having the single wavelength. For example, the capillary position measuring light source 127 is formed by a laser diode. The capillary 102 is irradiated with the light emitted from the capillary position measuring light source 127 in each capillary exchange, and the light reflected from the capillary 102 is detected with the optical detection unit 131. The image reflected from the capillary 102 is formed on the two-dimensional detector 136 to correctly measure a capillary position, which allows the position shift or inclination of the capillary 102 to be measured in capillary exchange.

When the position shift or inclination exists in the capillary 102, a fluorescence spectrum is displayed as being shifted on a screen of the two-dimensional detector 136. However, in the embodiment, the position shift or inclination of the capillary 102 is measured, so that the shift can be corrected in the fluorescence spectrum. Accordingly, the new spectral data acquisition is not required when the capillary is exchanged.

Figure 2:
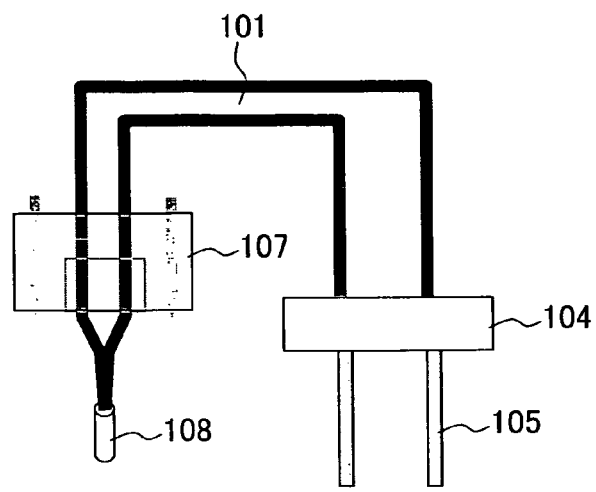
FIG. 2 is a perspective view schematically showing a capillary irradiation unit of the capillary electrophoresis apparatus.
Figure 2:
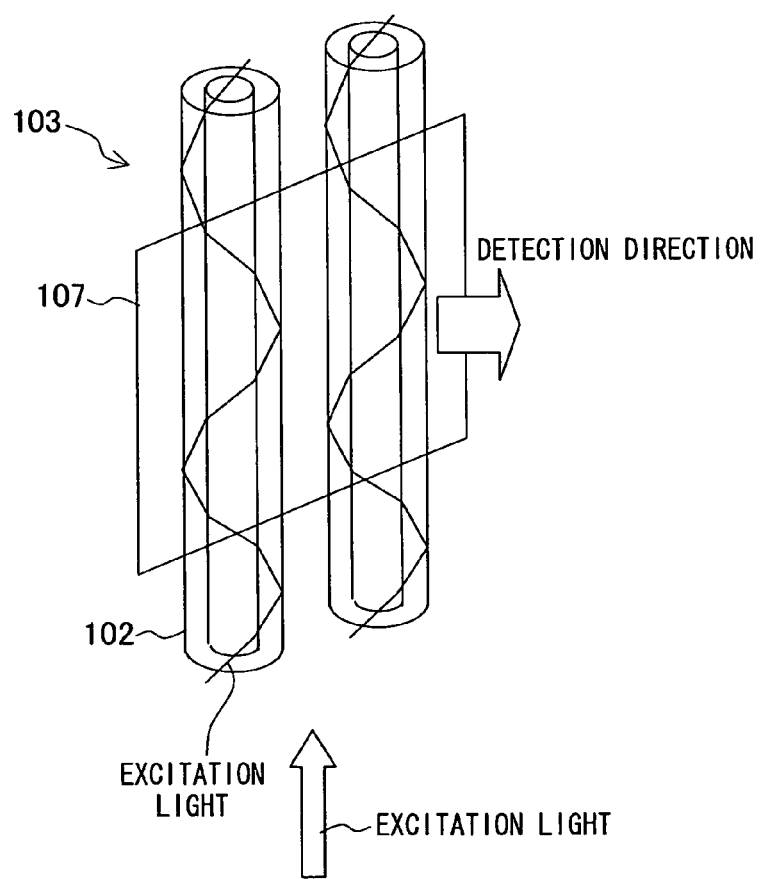

The irradiation unit 103 will be described in detail with reference to FIG. 2. As shown in FIG. 2A, the glass substrate 107 is provided at a position close to the capillary head 108. As shown in FIG. 2B, the plural capillaries 102 are arrayed on the glass substrate 107. The capillaries 102 are arranged on the glass substrate 107 in parallel with each other to some extent, and the capillaries 102 are arranged in substantially parallel to the glass substrate. The term "to some extent" means that the capillaries may be arranged to be inclined at the angle of several degrees, and the term "substantially" means that the inclination falls in an allowance degree of accuracy.

The excitation light is emitted from the optical irradiation unit 121 along the axis direction of the capillary 102, or the excitation light is emitted along the direction in which the excitation light is inclined at a predetermined angle with respect to the axis direction of the capillary 102. The polyimide coating of the capillary 102 is removed in the irradiation unit 103. Accordingly, the excitation light is totally reflected from outer surfaces of the plural capillaries 102, the excitation light propagates through the capillary 102 to simultaneously excite the samples in the capillaries 102. In the sample in the capillary 102, fluorescent light is emitted in a range of several millimeters to tens millimeters by the excitation light propagating through the capillary 102. Thus, the light emission region is linearly formed in the embodiment.

As shown in FIG. 1, the fluorescent light emitted from the sample in the capillary 102 is detected with the optical detection unit 131 arranged along the direction perpendicular to the axis direction of the capillary 102.

Figure 3:
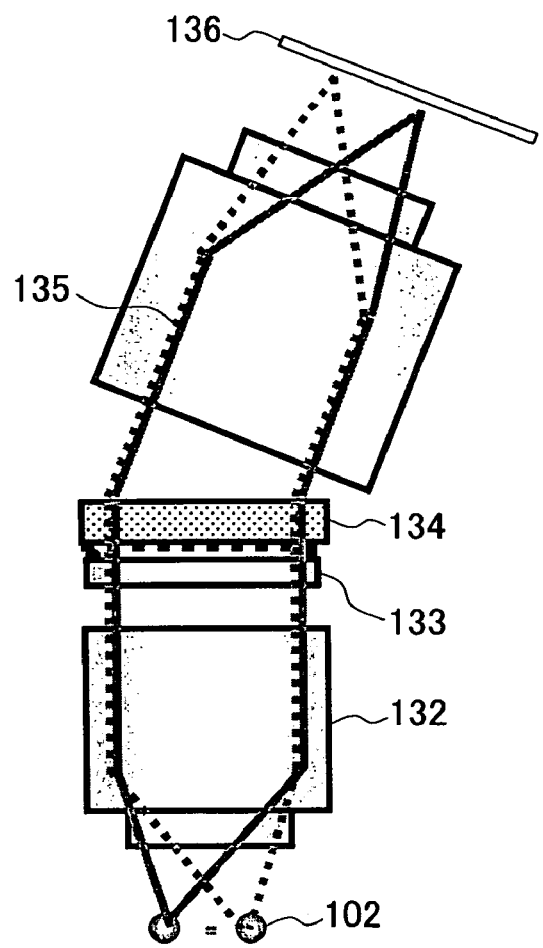
FIG. 3 is a perspective view schematically showing an optical detection unit of the capillary electrophoresis apparatus.
Figure 3:
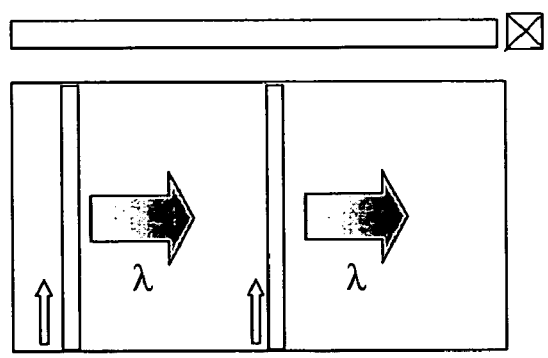

The optical detection unit 131 will be described with reference to FIG. 3. As shown in FIG. 3A, the optical detection unit 131 includes the first camera lens 132, the detection filter 133, the diffraction grating 134, the second camera lens 135, and the two-dimensional detector 136. In the embodiment, the diffraction grating 134 is used as the wavelength dispersive method. The fluorescent light emitted from the light emission region of the capillary 102 is formed in a parallel light flux by the first camera lens 132. The parallel light flux is introduced to the detection filter 133. Only the fluorescent light having the wavelength range used for the analysis is transmitted through the detection filter 133. The fluorescent light transmitted through the detection filter 133 is wavelength-dispersed by the diffraction grating 134, and the fluorescent light is focused on the two-dimensional detector 136 by the second camera lens 135. For example, the two-dimensional detector 136 is formed by a CCD camera. An image signal from the two-dimensional detector 136 is processed to analyze the sample with a computer.

FIG. 3B shows the image acquired by the two-dimensional detector 136. In the embodiment, the two images are acquired corresponding to the two capillaries. A horizontal axis of the image indicates a wavelength dispersive direction and a vertical axis indicates a capillary axis direction.

Alternatively, wavelength dispersion means in which prisms are appropriately combined may be used in place of the diffraction grating 134. In place of the CCD camera, the two-dimensional detector 136 may be formed by a one-dimensional detector, a photomultiplier, and a photodiode or the two-dimensional detector 136 may be formed by appropriately combining optical mechanisms.

The method, in which the capillary position is measured to correct the fluorescence spectrum shift based on the capillary position by the capillary electrophoresis apparatus according to the invention, will be described below. A data acquisition area is set in a first method. A standard fluorescence spectrum acquired as spectral data is corrected in a second method. In this case, the case where the one capillary is used while four-color fluorescent light dyes are used will be described.

Figure 4:
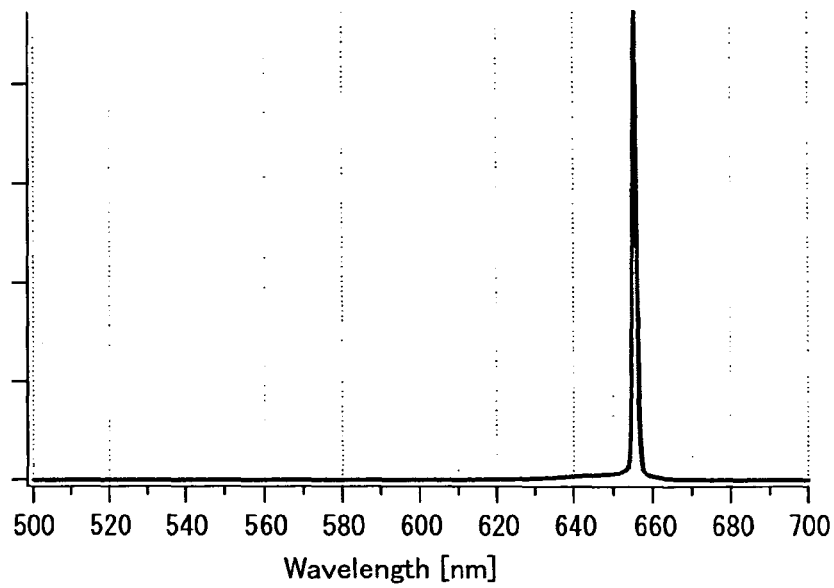
FIG. 4 shows wavelength characteristics of a capillary position measuring light source of the capillary electrophoresis apparatus.

FIG. 4 shows characteristics of a red laser diode. In the embodiment, the red laser diode is used as the capillary position measuring light source 127. The red laser diode is a monochromatic light source having a narrow light emission band in which a peak wavelength is 655 nm and a half value width is about 2 nm.

Figure 5:
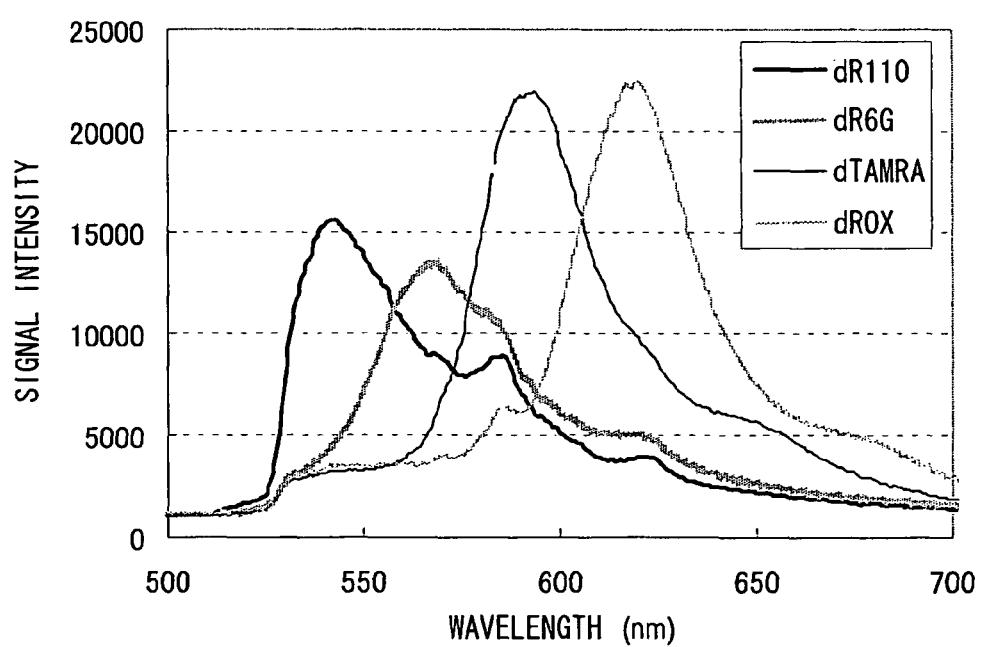
FIG. 5 shows a standard fluorescence spectrum which is acquired as spectral data of the capillary electrophoresis apparatus.

FIG. 5 shows a standard fluorescence spectrum which is acquired as spectral data. In this case, four-color fluorescent light dyes of dR110, dR6G, dTAMRA, and dROX are used. The spectra are obtained by the wavelength dispersion of the fluorescent light beams from the four-color fluorescent light dyes using the diffraction grating 134. The standard fluorescence spectra are used in the actual analysis. The four kinds of DNA can correctly be identified by separating the four-color fluorescence spectra from the detection light of the DNA sample.

The wavelength shift caused by the capillary position shift will be described with reference to FIG. 6. The fluorescence spectrum image position focused on the two-dimensional detector 136 is determined by a relative distance between the capillary 102 and the two-dimensional detector 136. It is assumed that the two-dimensional detector 136 is fixed. When the position of the capillary 102 is changed by the capillary exchange, the position of the fluorescence spectrum image is moved in parallel to a wavelength dispersive direction or a capillary axis direction although the shape of the fluorescence spectrum image on the image of the two-dimensional detector 136.

Figure 6:
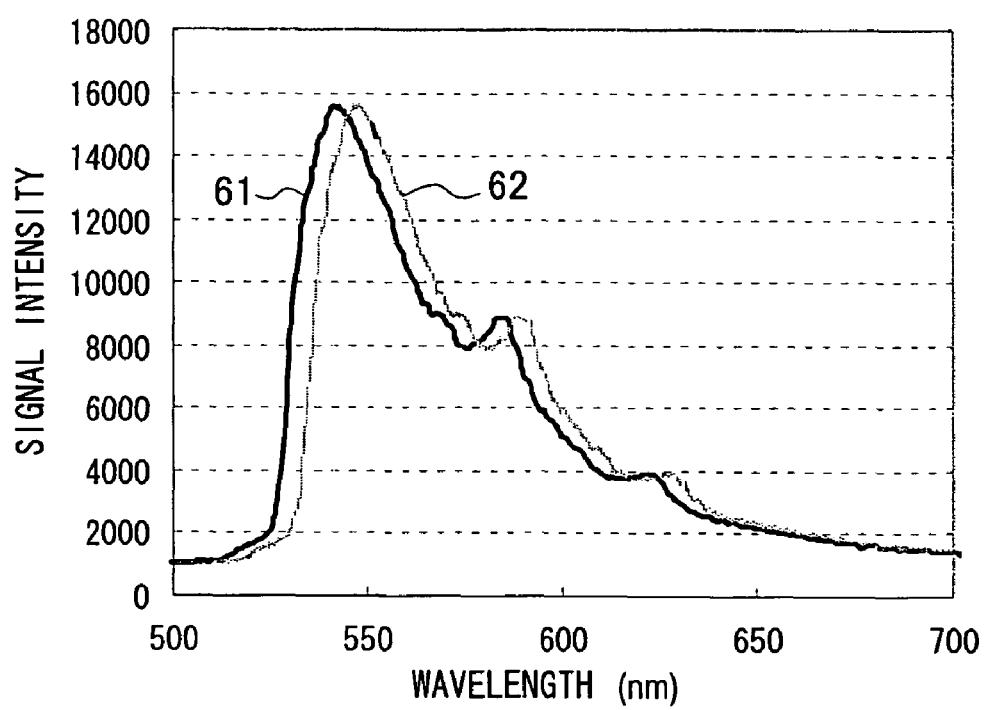
FIG. 6 is a graph for explaining fluorescence spectrum shift caused by capillary position shift in the capillary electrophoresis apparatus.

A bold curved line 61 of FIG. 6 expresses the fluorescence spectrum image which is focused on the two-dimensional detector 136 when the capillary 102 is located at a standard position. The standard position shall mean a position of the capillary 102 when the spectral data is acquired.

The vertical axis indicates signal intensity and the horizontal axis indicates a wavelength. However, a wavelength scale of the horizontal axis is set when the spectral data is acquired. Accordingly, the horizontal axis indicates a wavelength dispersive direction position in the image of the two-dimensional detector 136. A thin curved line 62 of FIG. 6 expresses the fluorescence spectrum image which is focused on the two-dimensional detector 136 when the position of the capillary 102 is moved in the wavelength dispersive direction. When the position of the capillary 102 is changed, the fluorescence spectrum image is shifted in the wavelength direction. This phenomenon is generated in the attachment and exchange of the capillary array 101.

The fluorescence spectrum from the DNA sample cannot correctly be separated, when the data is acquired to perform the analysis under the condition that the fluorescence spectrum image position is shifted in the analysis with respect to the standard fluorescence spectrum image position acquired as the spectral data. For example, in the case where the fluorescent light of the fluorescent light dye dR110 is detected, the fluorescent light signal of dR6G is generated as the pull-up signal to decrease the analysis reliability. With increasing fluorescence spectrum shift, the pull-up signal is increased to worsen the analysis accuracy.

On the contrary, in the invention, the position of the capillary 102 is correctly measured in the analysis, and a predetermined operation is performed such that the fluorescence spectrum image is not shifted with respect to the standard fluorescence spectrum image acquired as the spectral data. The specific operation will be described later.

Figure 7:
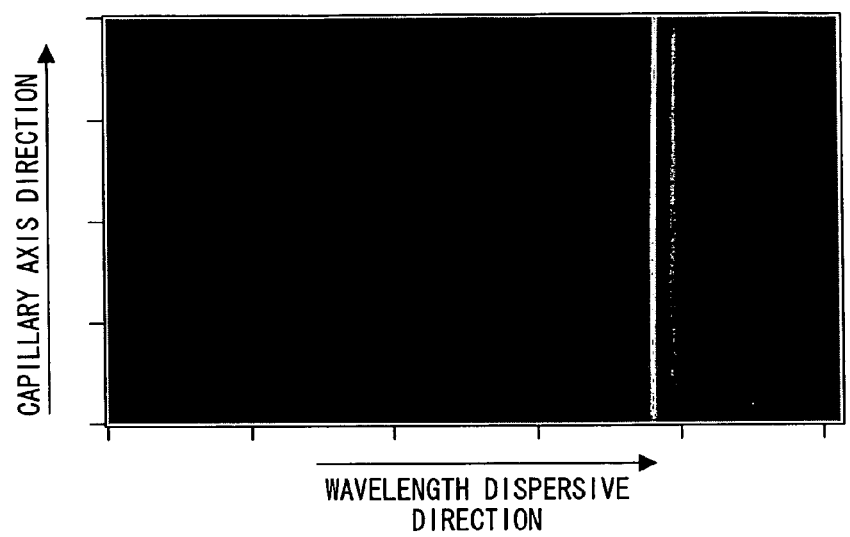
FIG. 7 shows an image example for detecting a capillary position in the capillary electrophoresis apparatus.
Figure 7:
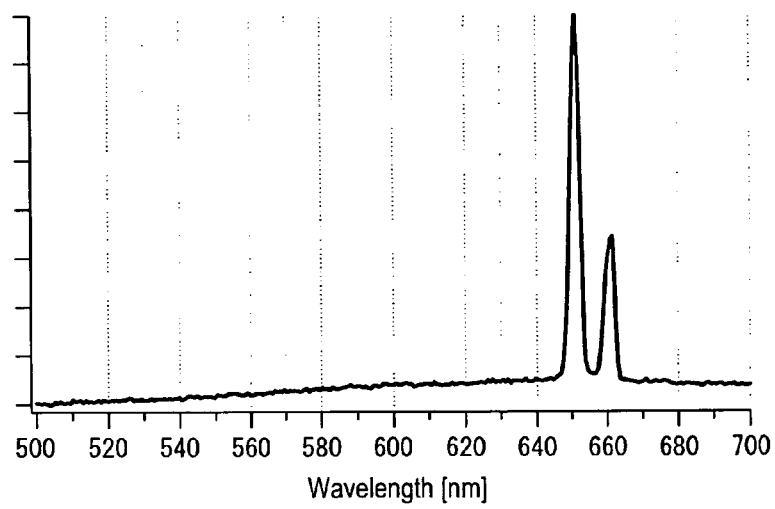

The method of measuring the capillary position will be described with reference to FIG. 7. FIG. 7A shows the capillary image on the image of the two-dimensional detector 136 when the capillary 102 is irradiated with the light from the capillary position measuring light source 127. In FIG. 7A, the vertical axis indicates a position in the capillary axis direction and the horizontal axis indicates a position in the wavelength dispersive direction. FIG. 7B shows the capillary image spectrum, the vertical axis indicates light intensity, and the horizontal axis indicates a wavelength. In the embodiment, the red laser diode which is of the light source having the single wavelength is used as the capillary position measuring light source 127. Accordingly, the image having the single wavelength and the spectrum are obtained even if the light reflected from the capillary 102 is dispersed by the diffraction grating 134. The two peaks in the spectrum of FIG. 7B expresses the light reflected from the outer surface of the capillary 102. The distance between the two peaks is equal to the outer diameter of the capillary 102.

The capillary having the outer diameter of 326 μm is used in the embodiment. The distance between the two peaks is about 330 μm. The wavelength indicating the capillary center position on the image of the two-dimensional detector 136 is obtained from the capillary image or spectrum of FIG. 7. In the embodiment, because the image having a certain length can be acquired in the capillary axis direction, not only the capillary position shift can correctly be measured, but also the inclination angle of the capillary can correctly be measured.

Figure 8:
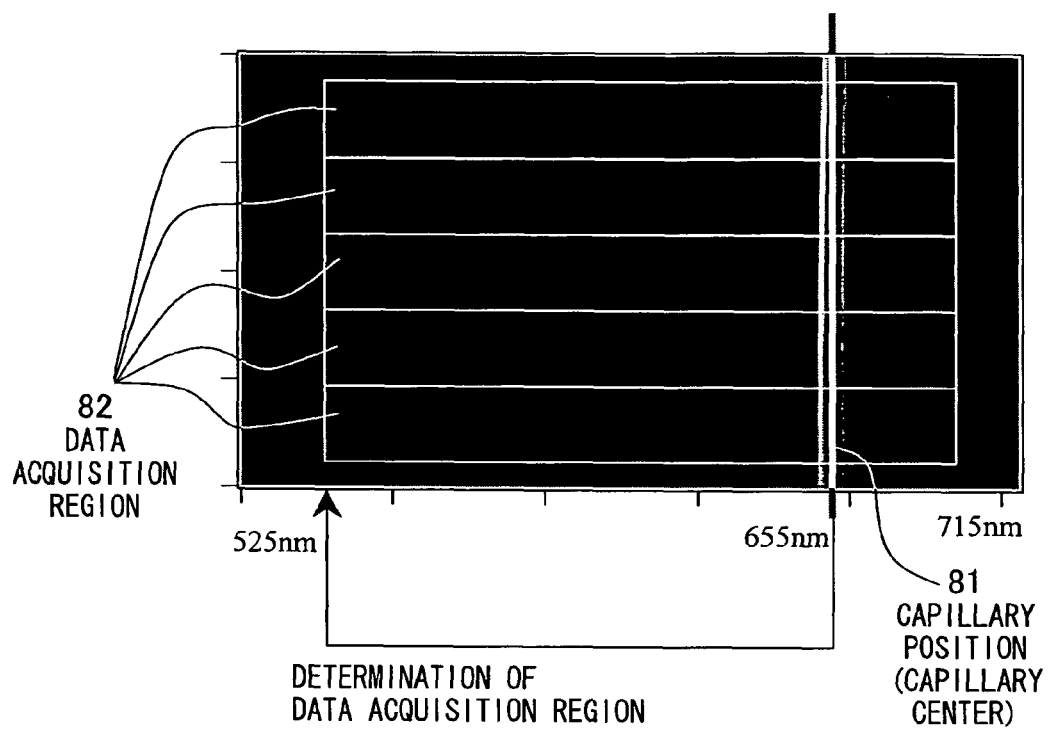
FIG. 8 shows a method of setting a data acquisition area in an image taken by a two-dimensional detector in the capillary electrophoresis apparatus.

The method of setting the data acquisition area on the image obtained by the two-dimensional detector 136 will be described below with reference to FIG. 8. Similarly to FIG. 7A, FIG. 8 shows a capillary image 81 on the image of the two-dimensional detector 136 when the capillary 102 is irradiated with the light from the capillary position measuring light source 127, the vertical axis indicating a position in the capillary axis direction, and the horizontal axis indicating a position in the wavelength direction on the image of the two-dimensional detector 136.

First, the method of setting a range in a crosswise direction of the data acquisition area will be described. As described above, the capillary center position is determined on the image of the two-dimensional detector 136 using the red laser diode which is of the capillary position measuring light source 127. The capillary center position expresses the wavelength of 655 nm of the capillary position measuring light source 127. That is, the position of the wavelength of 655 nm can be specified in the two-dimensional image obtained by the two-dimensional detector 136. The data acquisition area can be set on the two-dimensional detector 136 based on the wavelength of 655 nm.

In the analysis experiment, the analysis wavelength range is previously determined. It is assumed that the analysis wavelength ranges from 525 nm to 715 nm. The positions of the wavelengths of 525 nm and 715 nm are specified based on the position of the wavelength of 655 nm. It is assumed that CCD having resolution of one pixel equivalent to 2 nm is used as the two-dimensional detector 136. A difference between the wavelength of 655 nm and the wavelength of 525 nm is 130 nm, and the difference corresponds to 65 pixels. Therefore, the wavelength of 525 nm is expressed by the position which is shifted by 65 pixels leftward from the position of the wavelength of 655 nm. Similarly a difference between the wavelength of 655 nm and the wavelength of 715 nm is 60 nm, and the difference corresponds to 30 pixels. Therefore, the wavelength of 715 nm is expressed by the position which is shifted by 30 pixels rightward from the position of the wavelength of 655 nm. The analysis wavelength ranging from 525 nm to 715 nm corresponds to 95 pixels. That is, the data acquisition area on the two-dimensional detector 136 is set in the range from the position shifted by 65 pixels leftward from the position of the wavelength of 655 nm to the position shifted by 30 pixels rightward from the position of the wavelength of 655 nm. In this case, the analysis wavelength ranges from 525 nm to 715 nm. However, the data acquisition area is similarly determined even in other analysis wavelength ranges.

According to the invention, the data acquisition area on the two-dimensional detector 136 is set based on the wavelength of 655 nm of the capillary position measuring light source 127, so that the spectrum image can be obtained in the previously set analysis wavelength range.

When the range is set in the crosswise direction of the data acquisition area, the range is set in a lengthwise direction of the data acquisition area. The image region of the two-dimensional detector 136 is equally divided into plural regions by lines parallel to the horizontal axis. Five data acquisition areas 82 are set in the embodiment.

The first embodiment of the analysis method with the capillary electrophoresis apparatus of the invention will be described with reference to FIG. 9. FIG. 9A shows the case where the capillary 102 is located at the standard position. The standard position shall mean a position of the capillary when the spectral data is acquired. At the standard position, there is neither position shift nor inclination in the capillary 102. FIG. 9A shows an arrangement state of the capillary 102, an image 201 expressing a capillary image 91, and an image 202 expressing a standard fluorescence spectrum 92 acquired as the spectral data in the left-to-right order. The five data acquisition areas are set in the image 202.

FIG. 9B shows the case where the position of the capillary 102 is shifted from the standard position in the wavelength dispersive direction due to the capillary exchange. FIG. 9B shows the arrangement state of the capillary 102, an image 203 expressing a capillary image 93, and an image 204 expressing a fluorescence spectrum 94 of the analysis sample in the left-to-right order. The five data acquisition areas are set in the image 204. Because the position of the capillary image 91 in the image 201 of FIG. 9A differs from the position of the capillary image 93 in the image 203 of FIG. 9B, the position of the data acquisition area in the image 204 of FIG. 9B is shifted in the crosswise direction from the position of the data acquisition area in the image 202 of FIG. 9A.

FIG. 9C shows the case where the capillary 102 is inclined with respect to the capillary axis from the position in the spectral data acquisition due to the capillary exchange. FIG. 9C shows the arrangement state of the capillary 102, an image 205 expressing a capillary image 95, and an image 206 expressing a fluorescence spectrum 95 of the analysis sample in the left-to-right order.

In the case where the capillary 102 is inclined with respect to the capillary axis, it can be assumed that the capillary 102 consists of plural short portions and the portions are sequentially shifted in the wavelength dispersive direction. In the embodiment, the image is divided into five data acquisition area in the lengthwise direction. Accordingly, the capillary 102 is divided into five portions such that the five portions of the capillary 102 correspond to the five data acquisition areas, and it is assumed that each portion is shifted in the wavelength dispersive direction. However, in each portion, a shift amount becomes zero at the center position in the lengthwise direction of the image, and the shift amount is increased in the direction away from the center position.

FIG. 9D shows a graph 207 of a fluorescence spectrum 71 extracted from each data acquisition area. The five standard fluorescence spectra are acquired as the spectral data from the five data acquisition areas included in the image 202 of FIG. 9A. Similarly the five fluorescence spectra are acquired from the five data acquisition areas included in the image 204 of FIG. 9B. The five fluorescence spectra are acquired from the five data acquisition areas included in the image 206 of FIG. 9C. The five spectra of FIG. 9A become similar to the five spectra of FIG. 9B in each data acquisition area divided in the capillary axis direction. The pull-up signal is decreased, although the five spectra of FIG. 9A differ slightly from the five spectra of FIG. 9C depending on the number of portions divided in the lengthwise direction. As the number of divided portions is increased, the pull-up signal is decreased.

As described above, according to the invention, even if the capillary position shift is generated due to the capillary exchange, or even if the capillary is inclined due to the capillary exchange, the capillary position is measured, and the data acquisition area is set based on the measured capillary position. Therefore, the fluorescence spectrum is acquired at the same position as that of the standard fluorescence spectrum acquired as the spectral data. Accordingly, the spectral data acquisition is not required in each capillary exchange, and the pull-up signal can be prevented using the fluorescence spectrum acquired in the above-described manner.

In the light emission region of the capillary, sometimes thermal expansion is generated by the influence of the oven unit 161. Preferably the capillary position is measured immediately before the analysis data acquisition after the temperature is stabilized in the oven unit 161 and the capillary position is fixed.

The detailed operation procedure in the first embodiment of the analysis method with the capillary electrophoresis apparatus of the invention will be described with reference to FIG. 10. The spectral data is acquired in Step 200. Usually the spectral data acquisition is performed before shipment in a manufacturing plant. For example, the standard fluorescence spectra are acquired by electrophoresing the wavelength-calibrated DNA samples labeled by four-color fluorescent light dyes. When the standard fluorescence spectrum is acquired as the spectral data, the electrophoresis analysis is performed as follow.

The basic procedure of the electrophoresis analysis includes pre-analysis preparation of Step 201, analysis start of Step 202, filling of electrophoresis medium of Step 203, pre run of Step 204, sample introduction of Step 205, capillary position measurement and data region setting of Step 206A, electrophoresis of Step 207, and analysis of Step 208. The basic procedure of the electrophoresis analysis is performed on the user side.

An operator performs the pre-analysis preparation of Step 201. The capillary arrays 101 are exchanged when the capillary 102 is degraded or when the change in length of the capillary 102 is required. The buffer vessel 144 and the cathode buffer vessel 112 are filled with the buffer. A commercially available electrolyte fluid for electrophoresis can be cited as an example of the buffer. Then, the sample which is of the analysis target is dispensed into the wells of the sample vessel 143. For example, the sample is a polymerase chain reaction (PCR) product of DNA. The cleaning solution is dispensed in the cleaning vessel 145. For example, the cleaning solution is pure water. The electrophoresis medium is injected into the syringe 152. For example, the electrophoresis medium is a commercially available polyacrylamide resolving gel for electrophoresis.

The operator starts the analysis of Step 202. In the filling of electrophoresis medium of Step 203, the capillary 102 is filled with the new electrophoresis medium to form the electrophoresis path. The automatic sampler unit conveys the waste liquid vessel 146 immediately below the sample introducing unit 104. Then, the syringe 152 is driven to fill the capillary 102 with the new electrophoresis medium, and the used electrophoresis medium is disposed of in the waste liquid vessel 146. Finally, the automatic sampler unit conveys the cleaning vessel 145 immediately below the sample introducing unit 104, the sample introducing end 105 is dipped in the cleaning solution, and the sample introducing end 105 which becomes dirty with the electrophoresis medium is cleaned with cleaning solution.

In the pre run of Step 204, a predetermined voltage is applied to put the electrophoresis medium in the state suitable to the electrophoresis. The automatic sampler unit conveys the buffer vessel 144 immediately below the sample introducing unit 104, and the sample introducing end 105 is dipped in the buffer to form the electric current path. Then, the power supply unit applies the voltage ranging from several kilovolts to tens kilovolts to the electrophoresis medium for several minutes to tens minutes. Therefore, the electrophoresis medium is put into the state suitable to the electrophoresis. Finally, the automatic sampler unit conveys the cleaning vessel 145 immediately below the sample introducing unit 104, the sample introducing end 105 is dipped in the cleaning solution, and the sample introducing end 105 which becomes dirty with the buffer is cleaned with cleaning solution.

In the sample introduction of Step 205, the sample component is introduced into the electrophoresis path. The automatic sampler unit conveys the sample vessel 143 immediately below the sample introducing unit 104, and the sample introducing end 105 is dipped in the sample held in the wells of the sample vessel 143. Therefore, the electric current path is formed, and the sample component can be introduced into the electrophoresis path. The power supply unit applies the pulse voltage to the electric current path, and the sample component is introduced into the electrophoresis path. Finally, the automatic sampler unit conveys the cleaning vessel 145 immediately below the sample introducing unit 104, the sample introducing end 105 is dipped in the cleaning solution, and the sample introducing end 105 which becomes dirty with the sample is cleaned with the cleaning solution.

In Step 206A, the capillary position is measured and the data acquisition area is set. In the capillary position measurement, the capillary position is measured with the capillary position measuring light source 127. In the data acquisition area setting, the data acquisition area of the two-dimensional detector 136 is set based on the capillary position. The detailed process of Step 206A is described above with reference to FIG. 9.

In the electrophoresis of Step 207, each sample component contained in the sample is separated and analyzed by the electrophoresis. The automatic sampler unit conveys the buffer vessel 144 immediately below the sample introducing unit 104, the sample introducing end 105 is dipped in the buffer to form the electric current path. Then, the power supply unit applies the high voltage of about 15 kV to the electric current path to generate the electric field in the electrophoresis path.

The sample components in the electrophoresis path are moved to the irradiation unit 103 at speeds according to the characteristics of each sample component by the generated electric field. That is, the sample components are separated by the difference in migration velocity. The sample component reaching the irradiation unit 103 is sequentially detected. For example, in the case where the sample contains a large number of DNAs having different base lengths, the difference in migration velocity is generated by the base length, and DNA having the shorter base length first reaches the irradiation unit 103. The irradiation unit 103 irradiates the sample components with the excitation light. In each DNA, end of base sequences labeled by the fluorescent light emit the fluorescent light in the order in which the end of base sequence reaches the irradiation unit 103.

The two-dimensional detector 136 detects the fluorescence spectrum. The fluorescence spectrum is detected based on the data acquisition area set in Step 206A.

In the analysis of Step 208, the data acquired by the electrophoresis is normalized to acquire the target wavelength dispersive data by utilizing the spectral data acquired in Step 200. When the spectral data is incorrect, the pull-up signal is generated to decrease the reliability of the analysis result.

When the predetermined amount of data is taken, the process is ended. The voltage application is stopped to terminate the electrophoresis analysis. Thus, the sequence of analysis procedure is described above. In the case where the analysis is further performed, the analysis procedure is repeated from the filling of electrophoresis medium of Step 203. In the case where another analysis is performed, the analysis procedure is repeated from the pre-analysis preparation of Step 201. In both the cases, the spectral data acquisition of Step 200 is not repeated.

The second embodiment of the analysis method with the capillary electrophoresis apparatus of the invention will be described below with reference to FIG. 11. In the second embodiment, when the capillary position is changed due to the capillary exchange, the capillary position is measured, and the spectral data is corrected based on the measured capillary position. That is, the standard fluorescence spectrum is corrected in the spectral data acquisition in place of the data acquisition area. The corrected standard fluorescence spectrum is substantially equal to that of the spectral data which is acquired if the spectral data is newly acquired in the capillary exchange.

FIG. 11A shows the case where the capillary 102 is located at the standard position, namely, shows the capillary 102 in acquiring the spectral data. FIG. 11A shows the arrangement state of the capillary 102, an image 301 expressing a capillary image 91 and a standard fluorescence spectrum 92 acquired as the spectral data, and a graph 302 of a standard fluorescence spectrum 71 acquired from the image 301 in the left-to-right order.

The five data acquisition areas are set in the image 301. In the second embodiment, the data acquisition areas are fixed, and the data acquisition areas are not set based on the position of the capillary 102. For example, the five data acquisition areas are previously set on the image of the two-dimensional detector 136.

The standard fluorescence spectrum graphs are acquired from the data acquisition areas, and the standard fluorescence spectrum graphs are substantially equal to one another although the standard fluorescence spectrum graphs differ from one another in aberration of the optical system. Accordingly, the graph 302 shows one of graphs of the standard fluorescence spectra 71 acquired as the spectral data.

FIG. 11B shows the case where the position of the capillary 102 is shifted from the standard position toward the wavelength dispersive direction due to the capillary exchange. FIG. 11B shows the arrangement state of the capillary 102, an image 303 expressing a capillary image 93 and a fluorescence spectrum 94 of the analysis sample, and a graph 304 of a fluorescence spectrum 72 of the analysis sample acquired from the image 303, and a graph 305 of a fluorescence spectrum 73 of the post-correction analysis sample in the left-to-right order. The data acquisition area of the image 303 is same as the data acquisition area of the image 301.

The fluorescence spectrum graphs of the analysis samples are acquired from the data acquisition areas, and the fluorescence spectrum graphs of the analysis samples are substantially equal to one another although the fluorescence spectrum graphs of the analysis samples differ from one another in the aberration of the optical system. Accordingly, the graph 304 shows one of graphs of the fluorescence spectra 72 of the analysis samples.

The position of the fluorescence spectrum 72 shown by the graph 304 is shifted from the position of the standard fluorescence spectrum 71 shown by the graph 302. The shift amount of position between the fluorescence spectrum 72 and the standard fluorescence spectrum 71 corresponds to the shift amount of position between the capillary image 91 of the image 301 and the capillary image 93 of the image 303. The standard fluorescence spectrum 71 of the graph 302 is horizontally moved by the shift amount, which acquires the post-correction standard fluorescence spectrum 73 shown by the graph 305.

FIG. 11C shows the case where the position of the capillary 102 is inclined from the standard position with respect to the capillary axis due to the capillary exchange. FIG. 11C shows the arrangement state of the capillary 102, an image 306 expressing a capillary image 95 and a fluorescence spectrum 96 of the analysis sample, graphs 307 and 309 of fluorescence spectra 74 and 76 of the analysis sample acquired from the image 306, and graphs 308 and 310 of the fluorescence spectra 75 and 77 of the post-correction analysis sample in the left-to-right order. The data acquisition area of the image 306 is same as the data acquisition area of the image 301.

The fluorescence spectra 96 of the analysis samples in the five data acquisition areas are shifted according to the inclination of the capillary 102. The five fluorescence spectra are acquired from the five data acquisition areas, and the five fluorescence spectra are shifted from one another. The graph 307 shows the fluorescence spectrum acquired from the top-line data acquisition area and the graph 309 shows the fluorescence spectrum acquired from the last-line data acquisition area;

The position of the fluorescence spectrum 74 shown by the graph 307 is horizontally shifted from the position of the standard fluorescence spectrum 71 shown by the graph 302. The shift amount of position between the fluorescence spectrum 74 and the standard fluorescence spectrum 71 corresponds to the shift amount of position between the capillary image 91 of the image 301 and the capillary image 95 in the top-line data acquisition area of the image 306. The standard fluorescence spectrum 71 of the graph 302 is moved leftward by the shift amount, which acquires the post-correction standard fluorescence spectrum 75 shown by the graph 308.

Similarly, the position of the fluorescence spectrum 76 shown by the graph 309 is horizontally shifted from the position of the standard fluorescence spectrum 71 shown by the graph 302. The shift amount of position between the fluorescence spectrum 76 and the standard fluorescence spectrum 71 corresponds to the shift amount of position between the capillary image 91 of the image 301 and the capillary image 95 in the last-line data acquisition area of the image 306. The standard fluorescence spectrum 71 of the graph 302 is moved rightward by the shift amount, which acquires the post-correction standard fluorescence spectrum 77 shown by the graph 310.

However, because the capillary image 95 is inclined in each data acquisition area, the position of the capillary image 95 is acquired by determining the center position of the capillary image 95 in each data acquisition area.

Thus, in the second embodiment, the standard fluorescence spectrum acquired as the spectral data is corrected based on the capillary position shift amount of the inclination. The spectral data acquisition is not required in each capillary exchange because the analysis is performed with the post-correction standard fluorescence spectrum.

The generation of the pull-up signal can be prevented by utilizing the post-correction standard fluorescence spectrum for the process of analyzing the fluorescence spectrum acquired by the electrophoresis.

Figure 12:
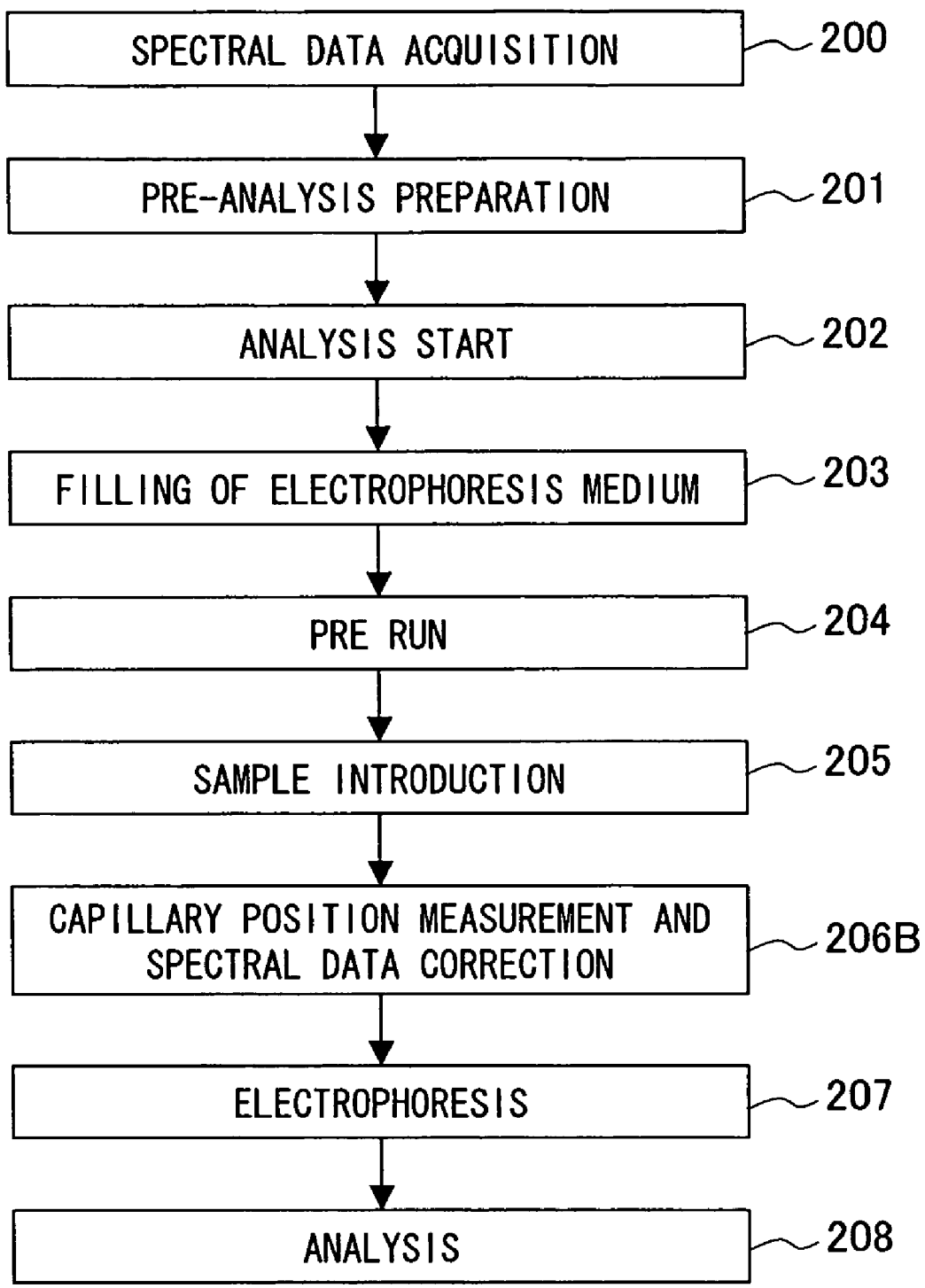
FIG. 12 shows a detailed operation procedure of the second embodiment of the analysis method in which the capillary electrophoresis apparatus is used.

The detailed operation procedure in the second embodiment of the analysis method with the capillary electrophoresis apparatus of the invention will be described with reference to FIG. 12. The spectral data is acquired in Step 200. Usually the spectral data acquisition is performed before shipment in a manufacturing plant. For example, the standard fluorescence spectra are acquired by electrophoresing the wavelength-calibrated DNA samples labeled by four-color fluorescent light dyes. When the standard fluorescence spectrum is acquired as the spectral data, the electrophoresis analysis is performed as follows.

The basic procedure of the electrophoresis analysis includes the pre-analysis preparation of Step 201, the analysis start of Step 202, the filling of electrophoresis medium of Step 203, the pre run of Step 204, the sample introduction of Step 205, capillary position measurement and spectral data correction of Step 206B, the electrophoresis of Step 207, and the analysis of Step 208. The basic procedure of the electrophoresis analysis is performed on the user side.

The pre-analysis preparation of Step 201, the analysis start of Step 202, the filling of electrophoresis medium of Step 203, the pre run of Step 204, the sample introduction of Step 205, and the electrophoresis of Step 207 are already described with reference to FIG. 10.

In Step 206B, the capillary position is measured and the spectral data is corrected. In the capillary position measurement, the capillary position is measured with the capillary position measuring light source 127. In the spectral data correction, the spectral data is corrected based on the capillary position.

In the analysis of Step 208, the data acquired by the electrophoresis is normalized to acquire the target wavelength dispersive data by utilizing the spectral data acquired in Step 206B.

Figure 13:
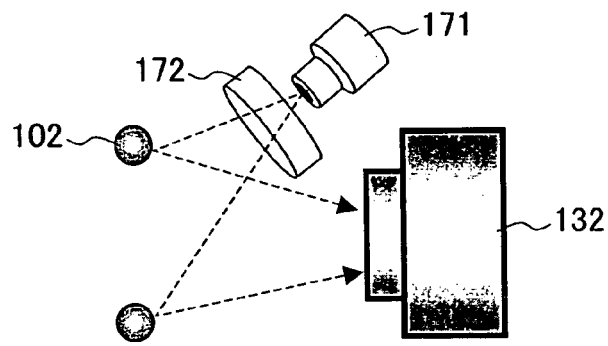
FIG. 13 shows another embodiment of the capillary position measuring light source of the capillary electrophoresis apparatus.
Figure 13:
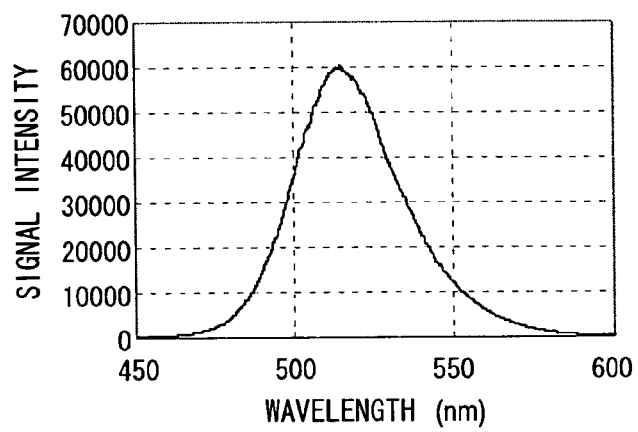
Figure 13:
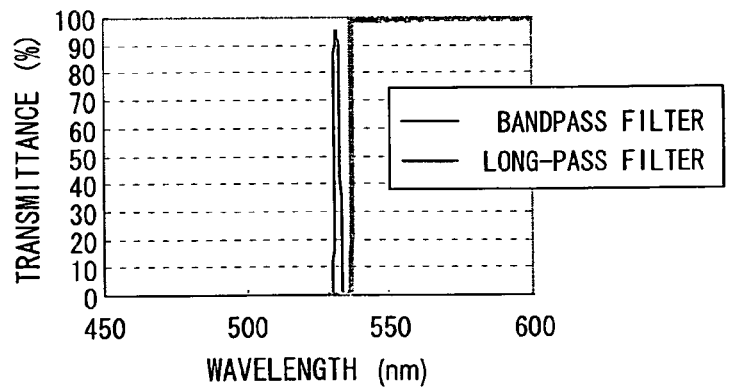

Another embodiment of the capillary position measuring light source will be described with reference to FIG. 13. A capillary position measuring light source 171 of FIG. 13 has a light emission wavelength band to some extent. Examples of the capillary position measuring light source 171 include a light emitting diode (LED) and a Ne lamp, or the like. As shown in FIG. 13A, a capillary position measuring filter 172 is provided on the output side of the capillary position measuring light source 171. The capillary position measuring filter 172 cuts a predetermined wavelength range in a light emission wavelength band of the capillary position measuring light source 171. The light transmitted through the capillary position measuring filter 172 is reflected from the surface of the capillary 102, and the light reaches the first camera lens 132.

FIG. 13B shows the light emission wavelength band of the capillary position measuring light source 171, and FIG. 13C shows transmission characteristics of the capillary position measuring filter 172. Because the filter characteristics are independent of the temperature, the filter characteristics are not influenced by the light source wavelength shift.

A bandpass filter which transmits the light through a predetermined narrow wavelength range may be used as the capillary position measuring filter 172, and a long-pass filter which transmits the light through a wavelength range wider than the predetermined wavelength range may be used as the capillary position measuring filter 172. In the case where the bandpass filter is used, the spectrum having the narrow wavelength range is acquired as shown in FIG. 7, so that the position of the capillary 102 can be specified from the position of the spectrum. In the case where the long-pass filter is used, the spectrum having the wavelength range wider than the predetermined wavelength position is acquired, so that the position of the capillary 102 can be specified from the start position of the spectrum.

Figure 14:
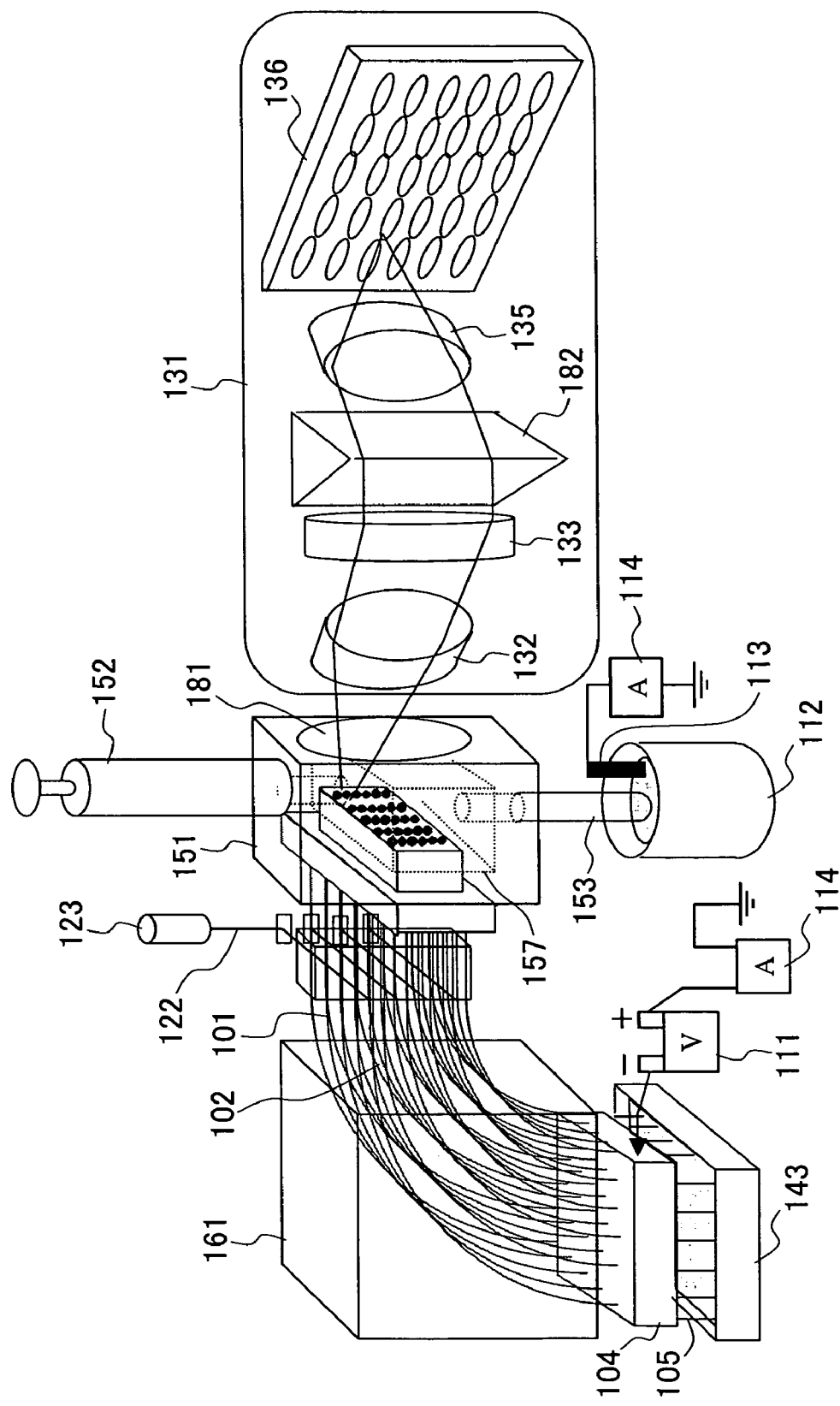
FIG. 14 is a perspective view schematically showing a capillary electrophoresis apparatus according to another embodiment of the invention.

A capillary electrophoresis apparatus according to another embodiment of the invention will be described with reference to FIG. 14. In the capillary electrophoresis apparatus of the embodiment, the fluorescent light from the light emission region of the capillary 102 is emitted from a tail end of the capillary. The optical detection unit 131 is arranged along the capillary axis line such that the fluorescent light can be detected from the tail end of the capillary.

The capillary 102 is irradiated with the excitation light 122 emitted from the light source 123, and the detection light is emitted from the tail end of the capillary. The detection light reaches the optical detection unit 131 through a detection window 181 of the pump unit 150.

The optical detection unit 131 of the embodiment includes the first camera lens 132, the detection filter 133, a prism 182, the second camera lens 135, and the two-dimensional detector 136. In the embodiment, the prism 182 is used as the wavelength dispersion device in place of the diffraction grating. The fluorescent light emitted from the tail end of the capillary 102 is formed in the parallel light flux by the first camera lens 132. The parallel light flux is guided to the detection filter 133. The detection filter 133 transmits only the fluorescent light having the wavelength range used for the analysis. The fluorescent light transmitted through the detection filter 133 is wavelength-dispersed by the prism 182, and the fluorescent light is focused on the two-dimensional detector 136 by the second camera lens 135. For example, the two-dimensional detector 136 is formed by the CCD camera. The image signal transmitted from the two-dimensional detector 136 is processed to analyze the sample with a computer.

In the capillary electrophoresis apparatus of this embodiment, sometimes the capillary position is also shifted due to the capillary exchange. However, the data acquisition area of the two-dimensional detector is set by the above-described method, or the standard fluorescence spectrum acquired as the spectral data is corrected by the above-described method. Therefore, the pull-up signal generation caused by the capillary position shift can be prevented.

The embodiments of the invention are described above. However, the invention is not limited to the above embodiments, but it is understood for those skilled in the art that various changes can be made without departing from the scope of the invention described in the claims. The appropriate combination of the embodiments should also be included in the invention.

What is claimed is:

1. A capillary electrophoresis apparatus comprising:
    an exchangeable capillary;
    an optical irradiation system including a light source which irradiates the capillary with excitation light;
    an optical detection system which has a wavelength dispersion device and a two-dimensional detector, the wavelength dispersion device dispersing fluorescent light from the capillary, the two-dimensional detector detecting a fluorescence spectrum image acquired from the wavelength dispersion device;
    a capillary position measuring light source which irradiates the capillary with a capillary position measuring light when the capillary is exchanged; and
    a filter including a band pass filter or long-pass filter positioned on the output side of the capillary position measuring light source,
    wherein when the capillary is configured to be irradiated with the light from the capillary position measuring light source, the two dimensional detector is configured to: detect a two-dimensional image of the capillary, set a plurality of data acquisition areas based on the position of the image of the capillary, and obtain a plurality of fluorescence spectrum images corresponding to a plurality of positions on the capillary from the plurality of data acquisition areas on the two-dimensional detector.

2. A capillary electrophoresis apparatus according to claim 1, wherein, when the capillary is shifted in the wavelength dispersive direction with respect to the standard position, the data acquisition areas are moved in the wavelength dispersive direction by a distance corresponding to the position deviation.

3. A capillary electrophoresis apparatus according to claim 1, wherein, when the capillary is inclined with respect to the standard position, the data acquisition areas are inclined at an angle corresponding to the inclination.

4. A capillary electrophoresis apparatus according to claim 1, wherein a wavelength scale is set in an image of the two-dimensional detector such that a wavelength of the capillary position measuring light source corresponds to an image position of the capillary by the two-dimensional detector, and a data acquisition area corresponding to a previously given analysis wavelength range is set by reading a long-wavelength edge and a short-wavelength edge of the analysis wavelength range using the wavelength scale.

5. A capillary electrophoresis apparatus comprising:
    an exchangeable capillary;
    an optical irradiation system including a light source which irradiates the capillary with excitation light;
    an optical detection system which has a wavelength dispersion device and a two-dimensional detector, the wavelength dispersion device dispersing fluorescent light from the capillary, the two-dimensional detector detecting a fluorescence spectrum image acquired from the wavelength dispersion device;

a capillary position measuring light source which irradiates the capillary with a capillary position measuring light when the capillary is exchanged; and a filter including a band pass filter or long-pass filter positioned on the output side of the capillary position measuring light source, wherein when the capillary is configured to be irradiated with the light from the capillary position measuring light source, the two-dimensional detector is configured to: detect a two-dimensional image of the capillary, obtain a plurality of fluorescence spectrum images corresponding to a plurality of positions on the capillary from a plurality of predetermined data acquisition areas on the two-dimensional detector, and correct a standard position of the fluorescence spectrum image which has been detected when the capillary was position at a standard position based on the position of the image of the capillary.

6. A capillary electrophoresis apparatus according to claim 1 or 5, wherein the plurality of data acquisition areas are arranged along a capillary axis direction, and each data acquisition area is defined by a range in a wavelength dispersive direction and a range in the capillary axis direction.

7. A capillary electrophoresis apparatus according to claim 1 or 5, wherein the capillary position measuring light source includes a light source having a single wavelength.

8. A capillary electrophoresis apparatus according to claim 1 or 5, wherein the capillary position measuring light source has:

a light source which has a predetermined light emission wavelength band.

9. A capillary electrophoresis apparatus according to claim 1 or 5, wherein the optical irradiation system irradiates the capillary with the excitation light from a direction along an axis line of the capillary or from a direction inclined at a predetermined angle with respect to the axis line of the capillary.

10. A capillary electrophoresis apparatus according to claim 1 or 5, wherein the optical irradiation system has a light emitting diode which is of an excitation light source.

11. A capillary electrophoresis apparatus according to claim 1 or 5, wherein the standard position is the capillary position in spectral data acquisition performed before shipment.

12. A capillary electrophoresis method in which a sample is electrophoresed in a capillary, the capillary is irradiated with excitation light emitted from a light source of an optical irradiation system, fluorescent light from the capillary is dispersed to generate a fluorescence spectrum, the fluorescence spectrum is detected by a two-dimensional detector, and the sample is analyzed based on the detection result, the capillary electrophoresis method including:

irradiating the capillary with a light emitted from a capillary position measuring light source and passed through a filter including a band pass filter or long-pass filter when the capillary is exchanged;

detecting an image of the capillary by the two-dimensional detector;

setting a plurality of data acquisition areas on the two-dimensional detector based on the position of the image of the capillary; and detecting a plurality of fluorescence spectrum images corresponding to a plurality of positions on the capillary from the plurality of data acquisition areas on the two-dimensional detector.

13. A capillary electrophoresis method in which a sample is electrophoresed in a capillary, the capillary is irradiated with excitation light emitted from a light source of an optical irradiation system, fluorescent light from the capillary is dispersed to generate a fluorescence spectrum, the fluorescence spectrum is detected by a two-dimensional detector, and the sample is analyzed based on the detection result, the capillary electrophoresis method including:

irradiating the capillary with a light emitted from a capillary position measuring light source and passed through a filter including a band pass filter or long-pass filter when the capillary is exchanged;

detecting an image of the capillary by the two-dimensional detector;

detecting a plurality of fluorescence spectrum images corresponding to a plurality of positions on the capillary from a plurality of predetermined data acquisition areas on the two-dimensional detector; and correcting a standard position of fluorescence spectrum image which has been detected when the capillary was positioned at the standard position based on the position of the image of the capillary.

* * * * *